United States Patent [19]

Shoesmith

[11] Plant 4,469

[45] Oct. 23, 1979

[54] CHRYSANTHEMUM NAMED FANTASY

[75] Inventor: Leonard H. Shoesmith, Westfield-Woking, England

[73] Assignee: Pan-American Plant Company, West Chicago, Ill.

[21] Appl. No.: 955,004

[22] Filed: Oct. 26, 1978

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new and distinct cultivar of chrysanthemum for greenhouse culture as a spray pot plant characterized by the dark pink color of the spoon-tipped ray florets comprising the flower head, each spoon-shaped portion of the ray florets extending from a narrow white stem. This plant is also characterized by its 9-week response with medium sized blooms having a relatively heavy pollen production and by its formation of about 5 to 7 lateral breaks when pinched.

1 Drawing Figure

BACKGROUND OF THE NEW PLANT

This new chrysanthemum variety originated as a seedling of unidentified plants growing in a random pollinated field of chrysanthemums maintained by me at Westfield-Woking, Surrey, England, in connection with my efforts to develop new and improved chrysanthemums for commercial exploitation. The present variety was selected from plants grown at West Chicago, Ill., from seeds developed by me in my greenhouse at said Westfield-Woking and the new plant was asexually reproduced under my direction by cuttings from the original selected plant and subsequently propagated, by vegetative cuttings, through several successive generations which demonstrated that the distinctive characteristics of the new variery hold true from generation to generation and appear to be firmly fixed. Present propagation is done at West Chicago, Ill., and at Cortez, Fla.

DESCRIPTION OF THE DRAWINGS

This new variety of chrysanthemum plant is illustrated by the accompanying drawings, of which the first sheet is a photographic rendition in full color showing a spray pot plant in full bloom, the colors shown being as nearly true as it is reasonably possible to obtain by conventional professional photographic procedures. The second sheet of drawings is a mechanical reproduction of a Xerographic copy of typical leaves of the instant variety showing their distinctive characteristics.

DESCRIPTION OF THE NEW PLANT

The following is a detailed description of my new variety of chrysanthemum plant with the color designations according to The R.H.S. Colour Chart published by The Royal Horticultural Society of London, England, in collaboration with The British Colour Council, the observations having been made in the Spring of 1978 of greenhouse plants grown at West Chicago, Ill.

THE PLANT

Origin: Seedling.

Parentage: Unidentified random pollinated chrysanthemum plants.

Classification:

*Botanic.*—*Chrysanthemum morifolium.*

*Commercial.*—Spray Pot Chrysanthemum.

Form: Perennial herbaceous bush.

Height: About 33 to 39 cm.

Growth: Vigorous, upright and terminal with good strength and normal branching.

Foliage: Abundant; about 7 to 9 leaves on 10 cm. of stem.

*Size of leaf.*—Length — about 5.3 to 11.4 cm. Width — about 3.5 to 6.4 cm.

*Shape of leaf.*—Lanceolate and lobed, slightly serrated.

*Venation.*—Pinnate.

*Color.*—Upper side — 147A. Under side — 147B.

*Petioles.*—About 1.3 to 2.9 cm. long.

THE BUD

Form: Globular.

Size:

Diameter.— About 10 to 12 mm.

*Depth.*—About 6 to 7 mm.

Opening rate: The bud opens slowly.

Color:

*When phyllaries first divide.*—70B, 70C.

*When florets begin to unfurl.*—78D.

Phyllaries: The receptacle bears many involucral spear-shaped and upstanding bracts.

*Color.*—Inside — 137A. Outside — 137B.

*Surface aspect.*—Pubescent.

Peduncle: Length — about 3.5 to 5.5 cm.

*Surface aspect.*—Pubescent.

*Strength.*—Erect and strong.

THE FLOWER

Recommended flowering: The year around with photoperiod control.

Response: 9 weeks as a spray pot plant.

Natural flowering season: October 25 to November 2.

Blooms: Flower type — Composite and single.

*Borne.*—As a head of many florets on a receptacle.

*Size.*—Medium. Diameter: about 6 to 8 cm. Depth: about 3.5 to 4.0 cm.

*Shape.*—Cup-shaped when bloom first opens remaining the same as the bloom matures.

Florets: Number — Numerous.

*Form.*—Spoon-tipped single borne on a narrow stem of about one-half the entire floret length.

| Color: | | May | June |
|---|---|---|---|
| | Upper side | 70B, 74C | 74D |
| | Reverse Side | 73D | 73D |

Tonality at 6 feet - 73A–73B.

*Firmness.*—Medium.
*Appearance.*—Very slight shine.
Effect of weather: None. Recommended for greenhouse culture only.
Persistence: Blooms hang on and dry.
Fragrance: Typical chrysanthemum.
Lasting quality:
*On plant.*—About 3 weeks.
*As cut flower.*—Not recommended.

REPRODUCTIVE ORGANS

Stamens: Number — 5, all with anthers.
*Arrangement.*—Syngenesious.
*Filaments.*—About 2 to 4 mm. long.
*Pollen.*—Color — Yellow.

Pistils: One to each ray and disc floret.
*Styles.*—About 4 to 6 mm. long.
*Stigmas.*—Color — Yellow.
*Ovaries.*—Inferior bicarpellate.

This cultivar of chrysanthemum is particularly characterized by the dark pink color of the spoon-shaped outer portion of each ray floret, which portion is carried by a narrow white stem extending from the flower receptacle; by the medium size of the blooms when grown on a spray pot plant and the relatively heavy pollen production; by the 9-week response as a spray pot; and by the production of about 5 to 7 breaks when pinched.

I claim:

1. The new cultivar of chrysanthemum, substantially as herein shown and described, characterized by the form and coloration of the ray florets of its composite and single blooms; its relatively heavy pollen production; and its 9-week photoperiodic response when grown as a spray pot plant.

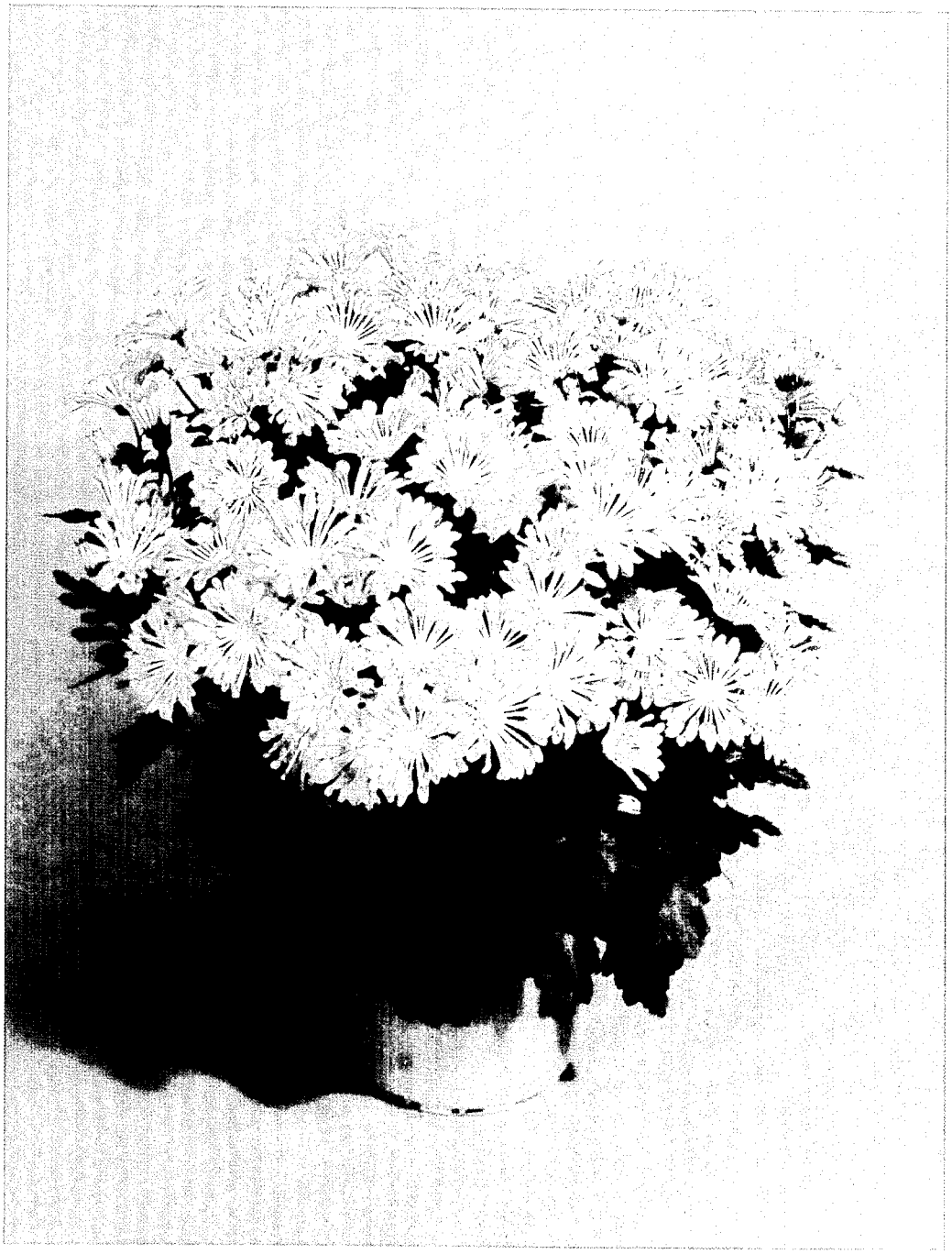

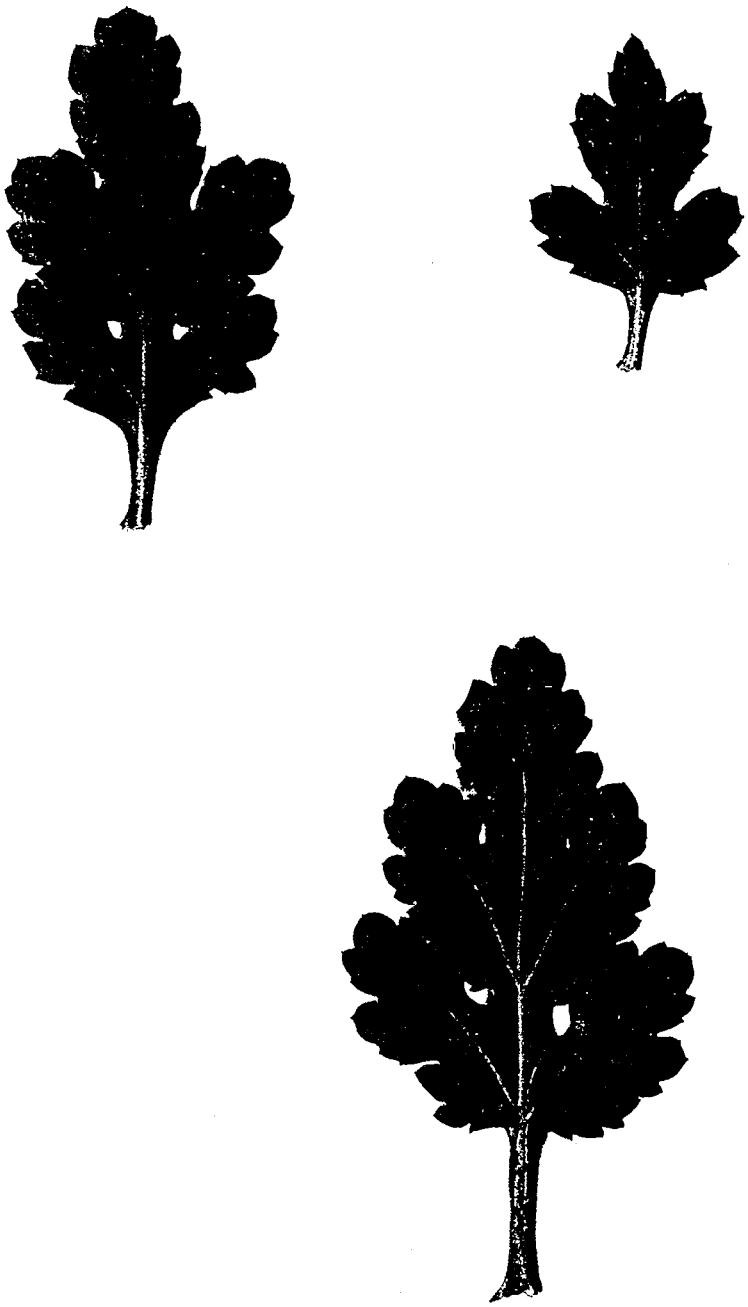

* * * * *